(12) United States Patent
Aronhime et al.

(10) Patent No.: US 7,473,804 B2
(45) Date of Patent: Jan. 6, 2009

(54) POLYMORPHS OF ATOMOXETINE HYDROCHLORIDE

(75) Inventors: Judith Aronhime, Rehovot (IL); Stefano Bianchi, Como (IT); Eugenio Castelli, Arlate di Calco (IT); Paola Daverio, Villasanta (IT); Silvia Mantovani, Cesano Maderno (IT); Adrienne Kovacsne-Mezei, Debrecen (HU)

(73) Assignee: Teva Pharmaceutical Fine Chemicals s.r.l., Bulciago (LC) (IT)

( * ) Notice: Subject to any disclaimer, the term of this patent is extended or adjusted under 35 U.S.C. 154(b) by 171 days.

(21) Appl. No.: 11/187,349

(22) Filed: Jul. 21, 2005

(65) Prior Publication Data

US 2006/0079581 A1  Apr. 13, 2006

Related U.S. Application Data

(60) Provisional application No. 60/590,851, filed on Jul. 22, 2004.

(51) Int. Cl.
*C07C 213/08* (2006.01)
*C07C 217/62* (2006.01)
*A61K 31/135* (2006.01)

(52) U.S. Cl. ........................ 564/354; 514/651
(58) Field of Classification Search .......... None
See application file for complete search history.

(56) References Cited

U.S. PATENT DOCUMENTS

| 4,018,895 A | 4/1977 | Molloy et al. |
| 4,777,291 A | 10/1988 | Misner |
| 4,868,344 A | 9/1989 | Brown |
| 5,658,590 A | 8/1997 | Heiligenstein et al. |
| 6,333,198 B1 | 12/2001 | Edmeades et al. |
| 6,541,668 B1 | 4/2003 | Kjell et al. |

FOREIGN PATENT DOCUMENTS

| DE | 41 23 253 A1 | 1/1993 |
| EP | 0 052 492 A1 | 5/1982 |
| EP | 0 193 405 A1 | 9/1986 |
| EP | 0 721 777 A2 | 1/1995 |
| EP | 1 798 215 A1 | 6/2007 |
| WO | WO 94/00416 | 1/1994 |
| WO | WO 00/58262 | 10/2000 |
| WO | WO 00/64855 | 11/2000 |
| WO | WO 2006/004923 A2 | 1/2006 |
| WO | WO 2006/004976 A2 | 1/2006 |
| WO | WO 2006/004977 A2 | 1/2006 |
| WO | WO 2006/004979 A2 | 1/2006 |
| WO | WO 2006/068662 A1 | 6/2006 |
| WO | WO-2007/068324 A1 | 6/2007 |

OTHER PUBLICATIONS

Srebnik, M. et al. "Chiral Synthesis via Organoboranes. 18. Selective Reductions. 43. Dissopinocampheylchloroborane as an Excellent . . . ." *J. Org. Chem.* (1988), vol. 53, p. 2916-2920.

Anon *(R)-(-)-N-Methyl-3-(2-Methylphenoxy)Phenyl-3-Phenylpropylamine (S)-(+)-Mandelate Chemical Abstracts Service XP-002367856 Dec. 29, 2004.

Koenig, T.M. et al. "A Convenient Method for Preparing Enantiomerically Pure Norfluoxetine, Fluoxetine and Tomoxetine" Tetrahedron Letters, vol. 35, No. 9, pp. 1339-1342 (1994).

Strobel, H.A.; Heineman, W.R., Chemical Instrumentation: A Systematic Approach, 3rd dd. (Wiley & Sons: New York 1989)—pp. 391-393, 879-894, 922-925, 953.

Snyder, L.R.; Kirkland, J.J., Introduction to Modern Liquid Chromatography, 2nd ed. (John Wiley & Sons: New York 1979)—p. 549-552, 571-572.

Sellers, J.A. et al. "Determination of the Enantiomer and Positional Isomer Impurities in Atomoxetine Hydrochloride with Liquid Chromatography Using Polysaccharide Chiral Stationary Phases." *J. of Pharmaceutical and Biomedical Analysis*, vol. 41, pp. 1088-1094 (2006).

Synthon BV, Research Disclosure, Atomoxetine hydrochloride polymoprhs, Nov. 2005.

Stephenson, Gregory A., et al., "Structural Determination of the Stable and Meta-Stable Forms of Atomoxetine HCl Using Single Crystal and Powder X-Ray Diffraction Methods", Journal of Pharmaceutical Sciences, Aug. 2006, vol. 95, No. 8, pp. 1677-1683.

Tomoxetine hydrochloride, 1998 JCPDS.

*Primary Examiner*—Brian J Davis
(74) *Attorney, Agent, or Firm*—Kenyon & Kenyon LLP

(57) ABSTRACT

The present invention provides novel crystalline polymorph forms of atomoxetine hydrochloride denominated Forms B and C and methods for their preparation, as well as methods for the preparation of Form A. The present invention provides pharmaceutical compositions that comprise atomoxetine hydrochloride Form B, Form C, or mixtures thereof that can be used to treat attention deficit/hyperactivity disorder.

34 Claims, 9 Drawing Sheets

POLYMORPHS OF ATOMOXETINE HYDROCHLORIDE

CROSS-REFERENCE TO RELATED APPLICATION

This application claims the benefit of provisional application Ser. No. 60/590,851, filed Jul. 22, 2004, which is incorporated herein by reference.

FIELD OF THE INVENTION

The present invention relates to crystalline polymorph forms of atomoxetine hydrochloride denominated Forms B and C as well as to methods for their preparation and use, and to methods for the preparation of Form A.

BACKGROUND OF THE INVENTION

Atomoxetine HCl is a selective norepinephrine reuptake inhibitor. It is marketed under the name STRATTERA® for the treatment of attention deficit/hyperactivity disorder (ADHD) and is available in 10 mg, 18 mg, 25 mg, 40 mg, and 60 mg dosage forms. It is a white to practically white solid, which has a solubility of 27.8 mg/ml in water.

Atomoxetine, chemically known as (R)(−)-N-methyl-3-(2-methylphenoxy)-3-phenylpropylamine; has the following structure:

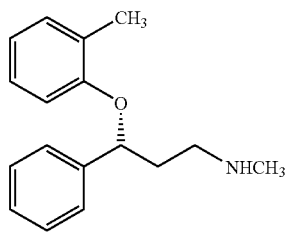

Atomoxetine, the (R)-(−) enantiomer of tomoxetine, is an aryloxyphenylpropylamine. It is about twice as effective as the racemic mixture and about nine times more effective than the (+)-enantiomer, as disclosed in U.S. Pat. No. 4,018,895, European Patent No. 0 052 492, and European Patent No. 0 721 777 (all by Eli Lilly and Co.)

Atomoxetine HCl may be obtained from tomoxetine that undergoes an optical resolution by any methods known in the art, such as crystallization with (S)-(+)-mandelic acid, disclosed, for example in EP Patent No. 0 052 492.

EP Patent No. 0 052 492 discloses a process for the preparation of atomoxetine HCl. In this process, (R)-(−)-tomoxetine (S)-(+)-mandelate is first basified in water to eliminate the mandelate, then extracted in diethyl ether. HCl gas is bubbled into the solution to obtain atomoxetime hydrochloride.

Similarly, U.S. Pat. No. 6,541,668 discloses a process for the preparation of atomoxetine HCl involving basifying the mandelate salt, followed by extracting with t-butyl methyl ether, removing water by azeotropic distillation, and adding hydrogen chloride.

Repetition of the processes disclosed in EP Patent No. 0 052 492 and U.S. Pat. No. 6,541,668 yielded a crystalline form of atomoxetine HCl, denominated Form A. Form A may be characterized by a powder x-ray diffraction pattern having peaks at about 13.7, 17.3, 18.7, 21.1, 22.6, 24.0, 27.3, 28.4 and 29.3±0.2 degrees two-theta, and further characterized by a powder x-ray diffraction pattern having peaks at about 8.5, 13.3, 13:7, 14.7, 17.9, 22.3, 25.0, 25.4, 25.7, 26.4, 29.8 and 32.0±0.2 degrees two-theta, substantially as depicted in FIG. 1. Form A obtained by these processes may also be characterized by an infrared absorption spectrum having peaks at about 2701, 1600, 1492, 1248, 769, 756 cm$^{-1}$, and further characterized by infrared absorption spectrum having peaks at about 3057, 2056, 2857, 2741, 2456, 2408, 1893, 1773, 1476, 1452, 1460, 1391, 1357, 1308, 1287, 1202, 1189, 1175, 1165, 1118, 1068, 1048, 1023, 1011, 933, 884, 821, 769, 705, 630, 579 and 546 cm$^{-1}$, substantially as depicted in FIG. 4. Form A may be further characterized by a Raman absorption spectrum substantially as depicted in FIG. 6.

Those skilled in the pharmaceutical arts understand that crystallization of an active pharmaceutical ingredient offers the best method for controlling important qualities like chemical quality, particle size, and polymorphic content. Thus, there is a need for crystal forms of atomoxetine hydrochloride and processes to produce such forms. The forms should be suitable for pharmaceutical use.

SUMMARY OF THE INVENTION

The present invention provides solid crystalline forms of atomoxetine as well their preparation.

The present invention provides processes for the preparation of crystalline atomoxetine hydrochloride Form A.

In one embodiment, Form A is prepared by a process comprising: combining atomoxetine hydrochloride Form B with acetone to obtain a mixture; and maintaining the mixture for a sufficient time to obtain atomoxetine hydrochloride Form A.

In another embodiment, the present invention provides a process for making atomoxetine hydrochloride Form A, comprising:
a) combining atomoxetine hydrochloride with water at a temperature of about 40 to about 60° C. to obtain a mixture;
b) cooling the mixture to room temperature to obtain a precipitate; and
c) recovering atomoxetine hydrochloride Form A.

In yet another embodiment, the present invention provides a process for making atomoxetine hydrochloride Form A, comprising:
a) combining atomoxetine hydrochloride with a solvent selected from water, methanol and a mixture of acetic acid and ethyl acetate, at a temperature ranging from room temperature to about 60° C. to obtain a mixture;
b) removing at least some of the solvent until a precipitate forms; and
c) recovering atomoxetine hydrochloride Form A.

In one embodiment, the present invention provides a process for making atomoxetine hydrochloride Form A, comprising:
a) combining atomoxetine base in a solvent selected from $C_{1-4}$ alcohol, $C_{2-4}$ alkyl ester, $C_{1-4}$ alkyl ether, mixtures thereof, and $C_{1-6}$ substituted or unsubstituted aromatic hydrocarbon to obtain a mixture;
b) combining the mixture with hydrochloric acid or hydrogen chloride to obtain a precipitate; and
c) recovering atomoxetine hydrochloride Form A from the precipitate.

Preferably, the solvent is selected from the group consisting of: isopropyl alcohol, methyl-t-butyl ether, ethyl acetate and mixtures thereof.

The present invention provides another crystalline form of atomoxetine hydrochloride, denominated Form B, characterized by data selected from: an x-ray powder diffraction pattern having peaks at about 11.5, 17.1, 19.8, 21.3, 22.5, 23.6, 24.6, 27.5 and 28.5±0.2 degrees two-theta; and an infrared absorption spectrum having peaks at about 2761, 1596, 1493, 1234, 768, and 711 cm$^{-1}$.

The present invention also provides a process for making atomoxetine hydrochloride Form B. This process comprises:
a) combining atomoxetine-(S)-(+)-mandelate with toluene and methanol to obtain a reaction mixture;
b) heating the reaction mixture to a temperature of about 60° C.;
c) combining the reaction mixture with gaseous hydrogen;
d) cooling the reaction mixture of step c) to a temperature of about 20° C. to about 25° C. for a sufficient amount of time for a slurry to form; and
e) recovering atomoxetine hydrochloride Form B from the slurry.

The present invention provides another process for making atomoxetine hydrochloride Form B. This process comprises:
a) combining atomoxetine hydrochloride in a solution of water and acetic acid;
b) heating the mixture to a temperature of about 40° C. to about 60° C. for a sufficient time to dissolve the atomoxetine hydrochloride; and
c) removing the acetic acid and water to form atomoxetine hydrochloride Form B.

Yet another crystalline form of atomoxetine hydrochloride is provided, denominated Form C. Atomoxetine hydrochloride Form C is characterized by an x-ray powder diffraction pattern having peaks at about 10.1, 16.4, 18.2 and 25.1±0.2 degrees two-theta.

The invention also provides a process for making atomoxetine hydrochloride Form C, comprising:
a) combining atomoxetine hydrochloride in a solution of water and acetone;
b) heating the mixture to a temperature of about 40° C. to about 60° C. for a sufficient time to dissolve the atomoxetine hydrochloride; and
c) removing the acetone and water to form atomoxetine hydrochloride Form C.

Pharmaceutical compositions comprising a therapeutically effective amount of atomoxetine hydrochloride Form B, and/or Form C and a pharmaceutically acceptable carrier are also provided. Also provided is a method for the treatment of attention deficit/hyperactivity disorder comprising administering to a human subject in need of such treatment the pharmaceutical compositions of the present invention.

DETAILED DESCRIPTION OF THE INVENTION

As used herein, "room temperature" or "RT" is meant to indicate a temperature of about 18-25° C., preferably about 20-25° C.

"Therapeutically effective amount" means the amount of a crystalline form that, when administered to a patient for treating a disease or other undesirable medical condition, is sufficient to have a beneficial effect with respect to that disease or condition. The "therapeutically effective amount" will vary depending on the crystalline form, the disease or condition and its severity, and the age, weight, etc., of the patient to be treated. Determining the therapeutically effective amount of a given crystalline form is within the ordinary skill of the art and requires no more than routine experimentation.

Figure 9:
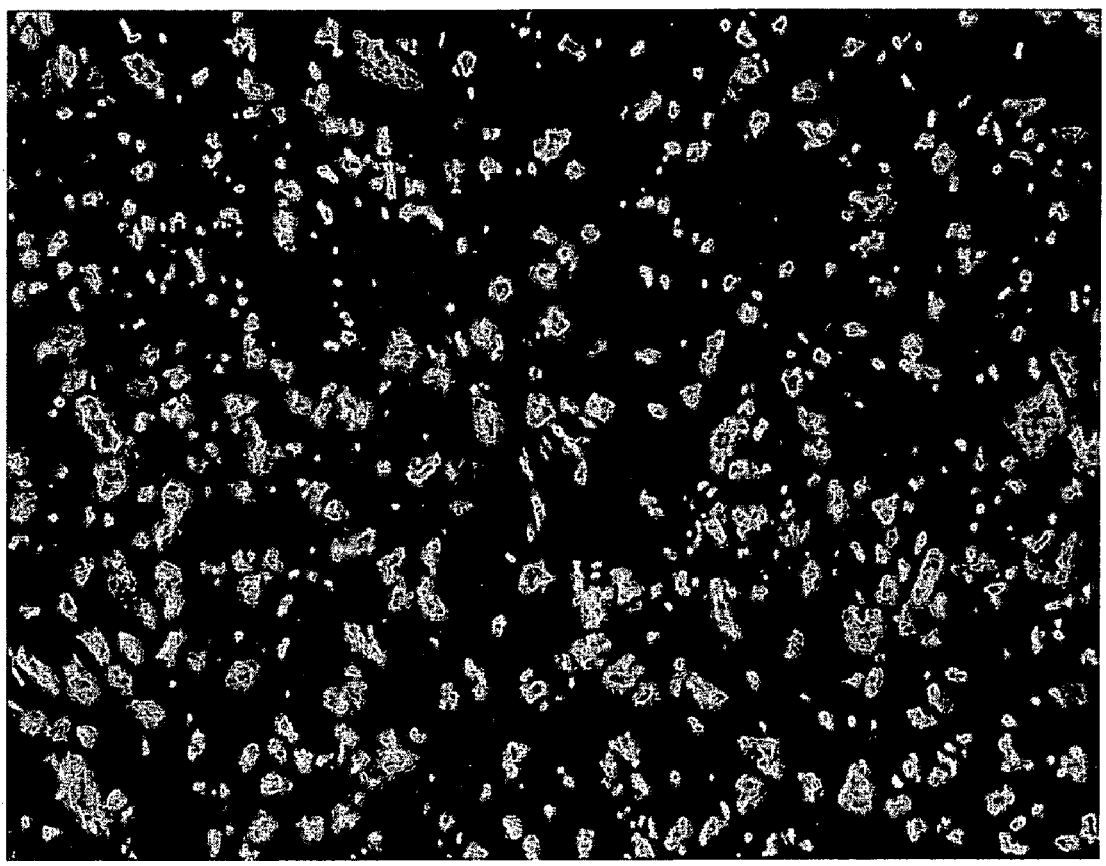
FIG. 9 is a photomicrograph of atomoxetine hydrochloride Form A.

The present invention provides processes for the preparation of the crystalline atomoxetine hydrochloride denominated Form A. Form A may be characterized by a powder x-ray diffraction pattern and an infrared absorption spectrum as described above. Form A has a particle size of about 35 um or less, as can be seen in FIG. 9.

One process for preparing Form A comprises combining atomoxetine hydrochloride Form B with acetone to obtain a mixture, and maintaining the mixture for a sufficient time to obtain atomoxetine hydrochloride Form A.

Preferably, the mixture is maintained for about 20 hours, but the mixture may be maintained for shorter times as well. Preferably, the reaction is performed at room temperature.

The present invention further provides a process for making atomoxetine hydrochloride Form A comprising combining atomoxetine hydrochloride with water at a temperature of about 40 to about 60° C. to obtain a mixture, and precipitating atomoxetine hydrochloride Form A.

Preferably, the atomoxetine hydrochloride and water are heated to a temperature of about 50°. Atomoxetine hydrochloride Form A may be precipitated by cooling the mixture to room temperature until a precipitate is formed, and then recovering atomoxetine hydrochloride Form A.

Atomoxetine hydrochloride may be recovered by any means known in the art, such as filtering out the solvent, washing the filtered solids, and drying of the solid.

The present invention provides another process for making atomoxetine hydrochloride Form A comprising:
a) combining atomoxetine hydrochloride with a solvent selected from water, methanol, and a mixture of acetic acid and ethyl acetate, at a temperature ranging from room temperature to about 60° C. to obtain a mixture;
b) removing at least some of the solvent until a precipitate forms; and
c) recovering atomoxetine hydrochloride Form A.

Preferably, the mixture in step a) is heated to a temperature of about 50°. Preferably, the ratio of the acetic acid:ethyl acetate mixture is 1:2. The solvent may be removed by any method known in the art, preferably by distillation.

Atomoxetine hydrochloride Form A may be recovered as described above.

The present invention provides yet another process for making atomoxetine hydrochloride Form A comprising:
a) combining atomoxetine base in a solvent selected from $C_{1-4}$ alcohol, $C_{2-4}$ alkyl ester, $C_{1-4}$ alkyl ether, mixtures thereof, and $C_{1-6}$ substituted or unsubstituted aromatic hydrocarbon to obtain a mixture;
b) combining the mixture with hydrochloric acid or hydrogen chloride to obtain a precipitate; and c) recovering atomoxetine hydrochloride Form A from the precipitate.

A $C_{1-4}$ alcohol includes methanol, ethanol or isopropanol. A $C_{2-4}$ alkyl ester includes methyl acetate, ethyl acetate, n-butyl acetate or iso-butyl acetate. A $C_{1-4}$ alkyl ether includes methyl t-butyl ether. A $C_{1-6}$ substituted or unsubstituted aromatic hydrocarbon includes toluene or xylene.

Preferably, the solvent is selected from the group consisting of: isopropyl alcohol, methyl-t-butyl ether, ethyl acetate and mixtures thereof. The atomoxetine hydrochloride Form A may be obtained as described above.

Figure 1:
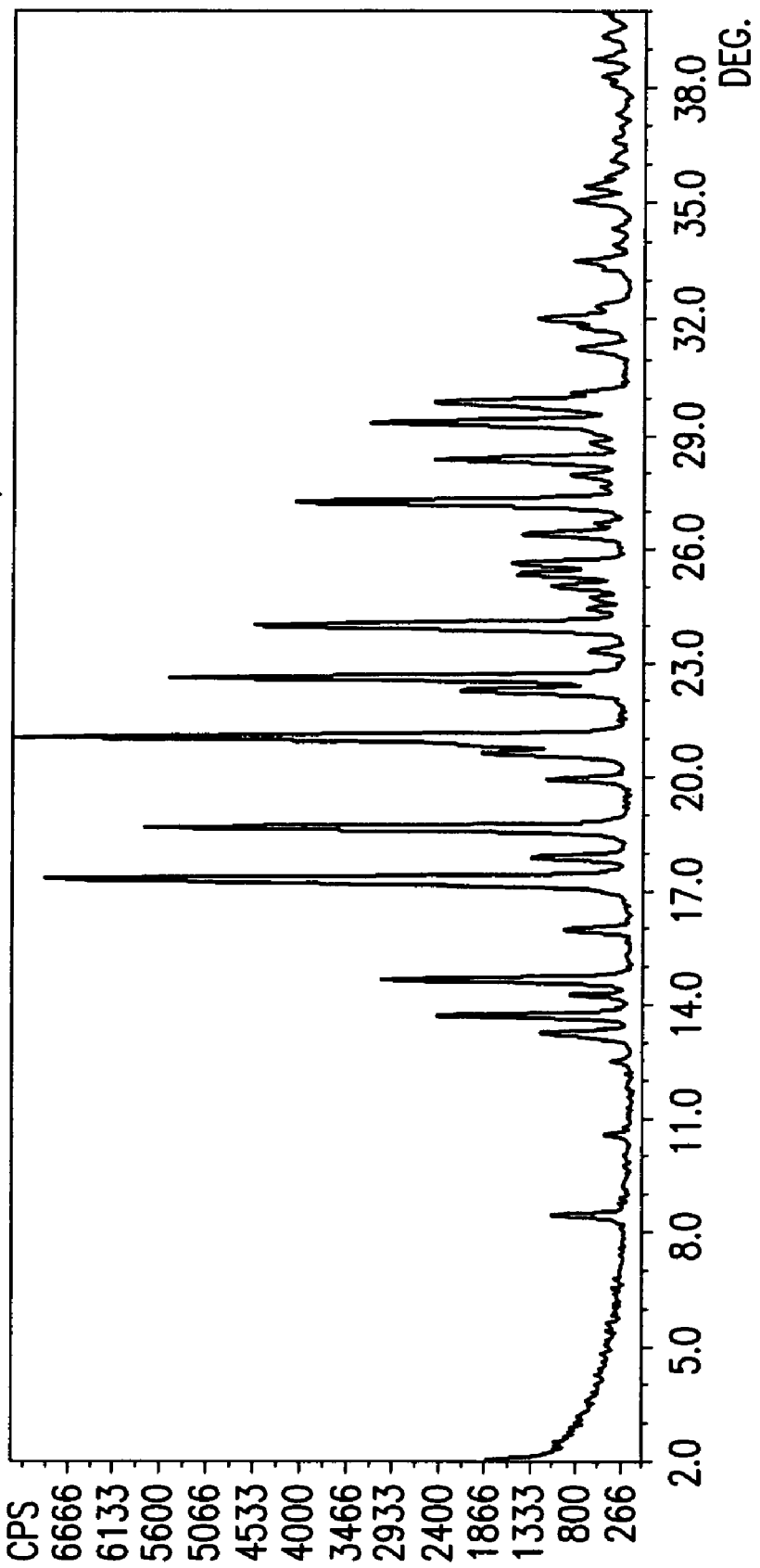
FIG. 1 is a characteristic powder x-ray diffraction spectrum of atomoxetine hydrochloride Form A.
Figure 2:
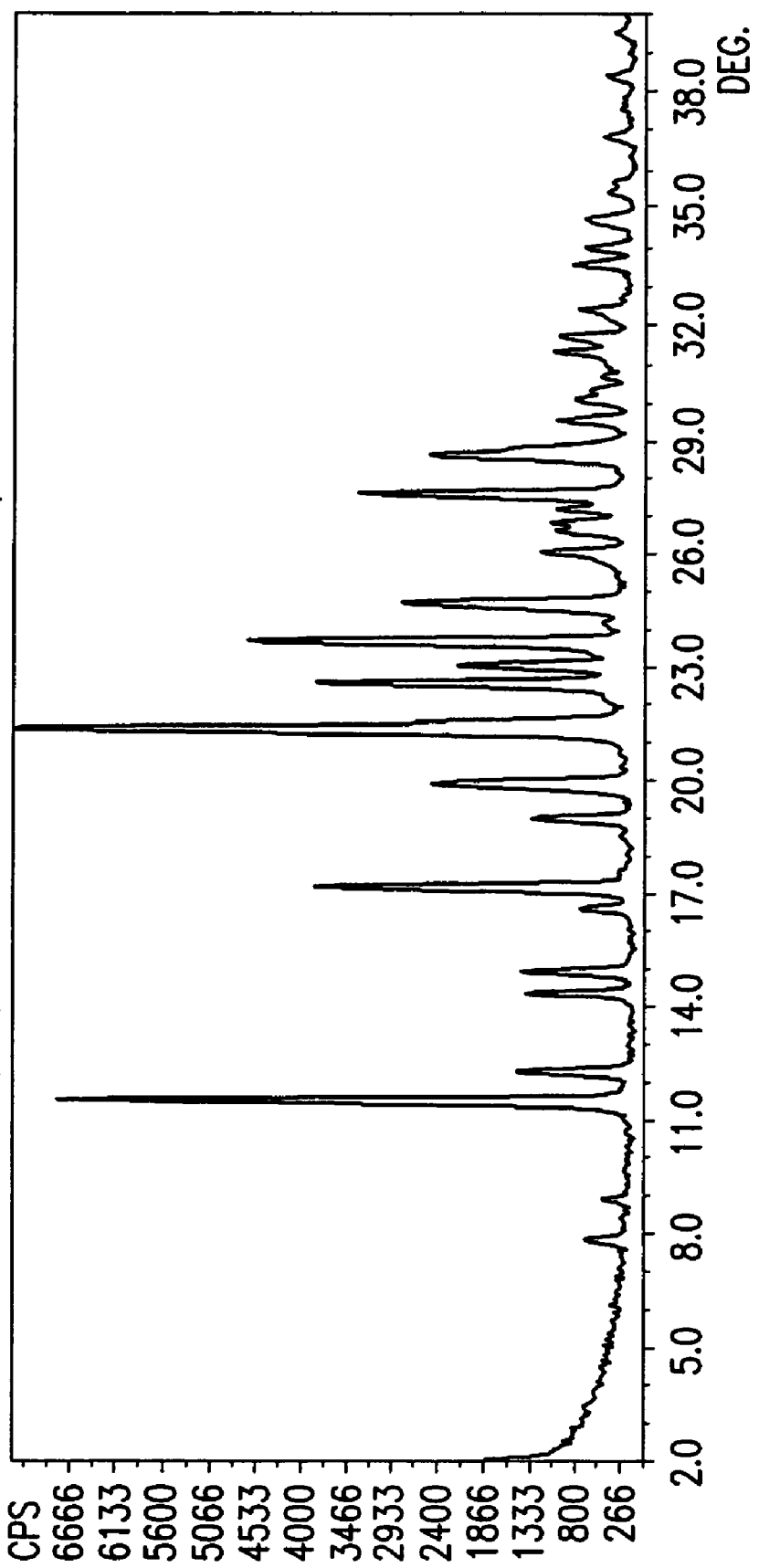
FIG. 2 is a characteristic powder x-ray diffraction spectrum of atomoxetine hydrochloride Form B.
Figure 5:
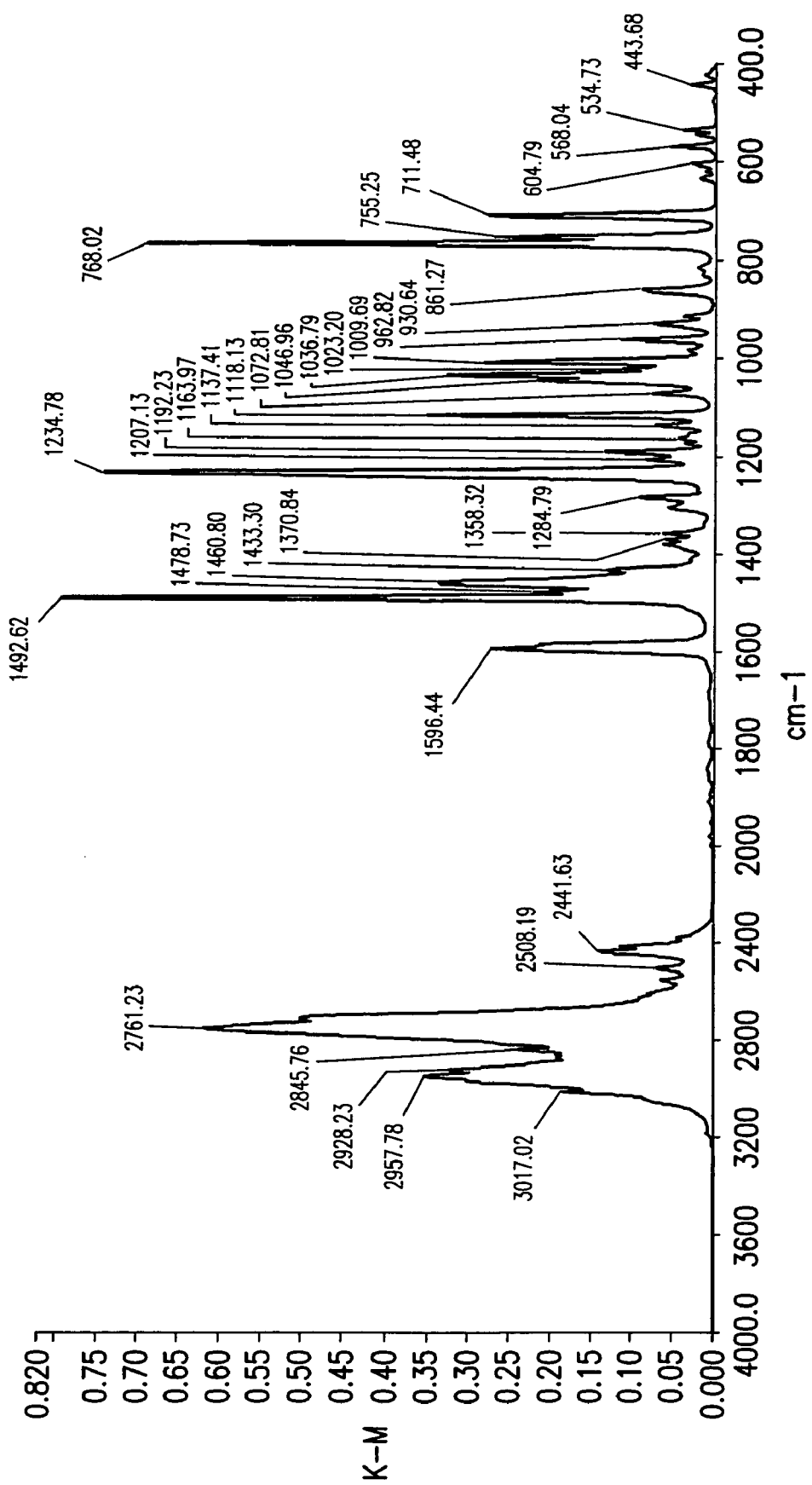
FIG. 5 is a characteristic infrared (IR) absorption spectrum of atomoxetine hydrochloride Form B
Figure 6:
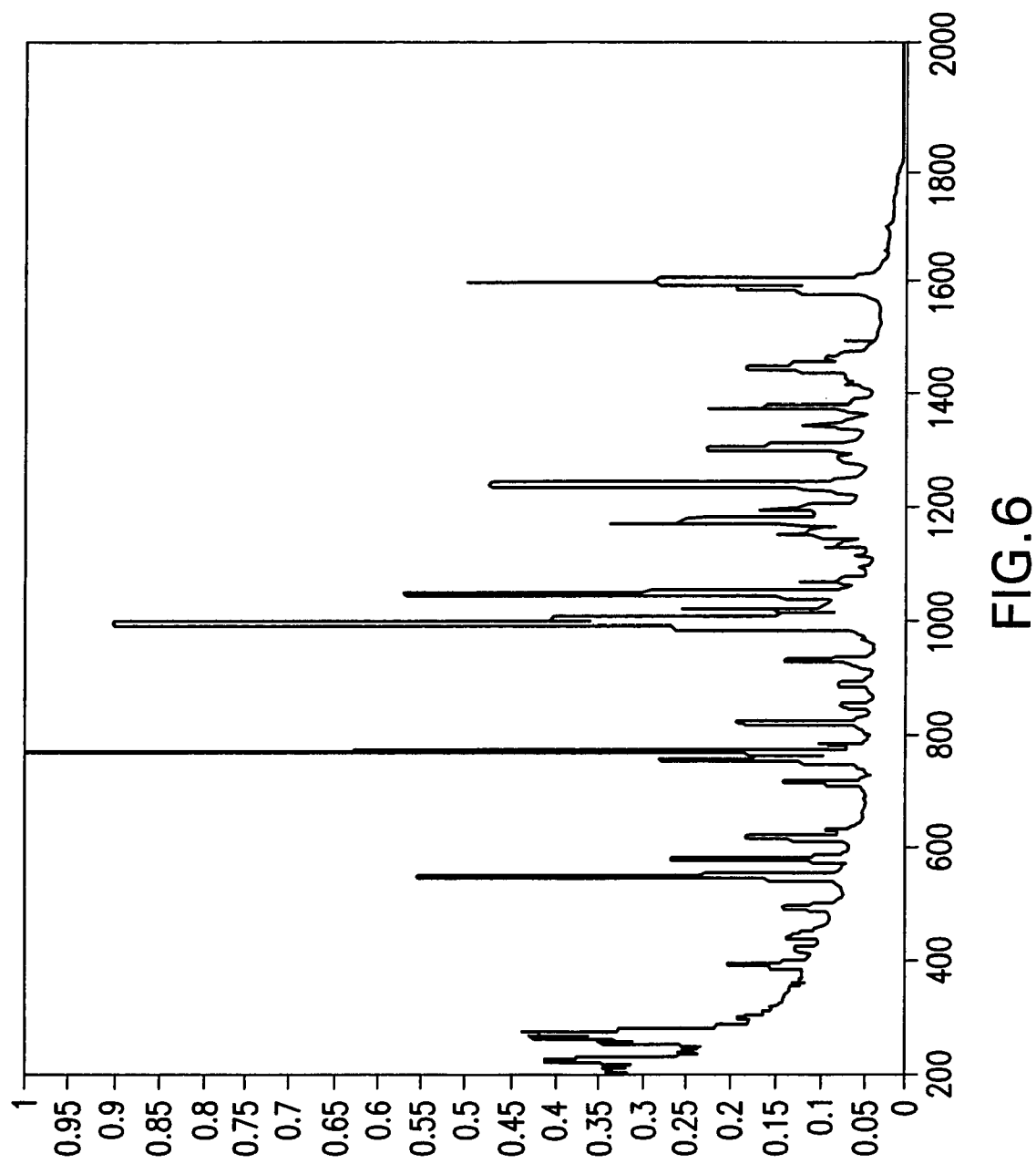
FIG. 6 is a characteristic Raman absorption spectrum of atomoxetine hydrochloride Form A.
Figure 7:
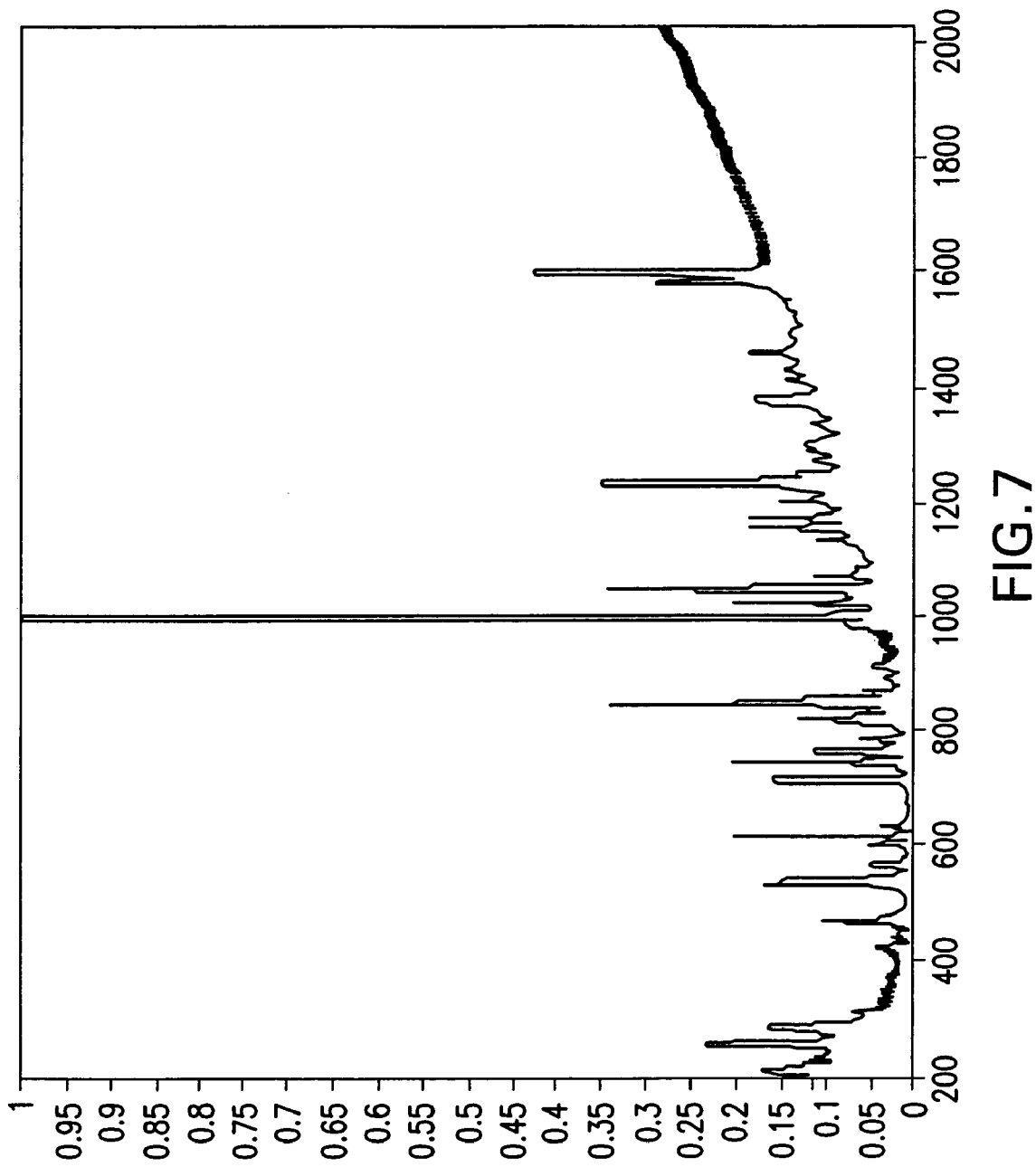
FIG. 7 is a characteristic Raman absorption spectrum spectrum of atomoxetine hydrochloride Form B.

The present invention provides a crystalline form of atomoxetine hydrochloride, denominated Form B, characterized by data selected from: an x-ray powder diffraction pattern having peaks at about 11.5, 17.1, 19.8, 21.3, 22.5, 23.6, 24.6, 27.5 and 28.5±0.2 degrees two-theta; and an infrared absorption spectrum having peaks at about 2761, 1596, 1493, 1234, 768, and 711 $cm^{-1}$. Form B may be further characterized by an x-ray powder diffraction pattern having peaks at about 7.8, 8.9, 12.2, 14.3, 14.9, 18.7, 26.0, 29.4, 29.9 and 31.2±0.2 degrees two-theta, substantially as depicted in FIG. 2. Form B may also be characterized by an infrared absorption spectrum having the following additional peaks at about 3017, 2958, 2928, 2845, 2508, 2442, 1479, 1460, 1433, 1371, 1358, 1285, 1207, 1192, 1175, 1164, 1137, 1118, 1072, 1047, 1037, 1023, 1010, 963, 931, 861, 755, 605, 568 and 535 $cm^{-1}$, substantially as depicted in FIG. 5. Form B may be further characterized by a Raman absorption spectrum substantially as depicted in FIG. 7.

Atomoxetine hydrochloride Form B may be further characterized by a melting point at about 163° C. The DSC thermogram of atomoxetine hydrochloride Form B shows a sharp endothermic melting peak and an exothermic peak due to decomposition at about 210° C. Thermal weight change measurements indicated a weight loss of about 2.6%.

Atomoxetine hydrochloride Form B may be substantially free of Form A. In certain embodiments, Form B contains less than about 10%, preferably less than about 5%, and even more preferably less than about 1% (by weight) of Form A.

Atomoxetine hydrochloride Form B may be substantially free of Form C. In certain embodiments, Form B contains less than about 10%, preferably less than about 5%, and even more preferably less than about 1% (by weight) of Form C.

The present invention also provides a process for making atomoxetine hydrochloride Form B. This process comprises:
a) combining atomoxetine-(S)-(+)-mandelate with toluene and methanol to obtain a reaction mixture;
b) heating the reaction mixture to a temperature of about 60° C.;
c) combining the reaction mixture with gaseous hydrogen chloride;
d) cooling the reaction mixture of step c) to a temperature of about 20° C. to about 25° C. for a sufficient amount of time for a slurry to form; and
e) recovering atomoxetine hydrochloride Form B from the slurry.

Preferably, the atomoxetine hydrochloride Form B is recovered by further cooling the slurry of step d) to about 0° C., and then the solid is separated from the solvents by any method known in the art, such as described above.

The present invention provides another process for making atomoxetine hydrochloride Form B. This process comprises:
a) combining atomoxetine hydrochloride in a solution of water and acetic acid;
b) heating the mixture to a temperature of about 40° C. to about 60° C. for a sufficient time to dissolve the atomoxetine hydrochloride; and
c) removing the acetic acid and water to form atomoxetine hydrochloride Form B.

Preferably, the mixture is heated in step b) to a temperature of about 50° C. Preferably, the mixture in step b) is maintained for at least 2 hours. Preferably, the ratio of the water and acetic acid in the solution of step a) is 2:1. The acetic acid and water may be removed from the mixture by evaporation.

Figure 3:
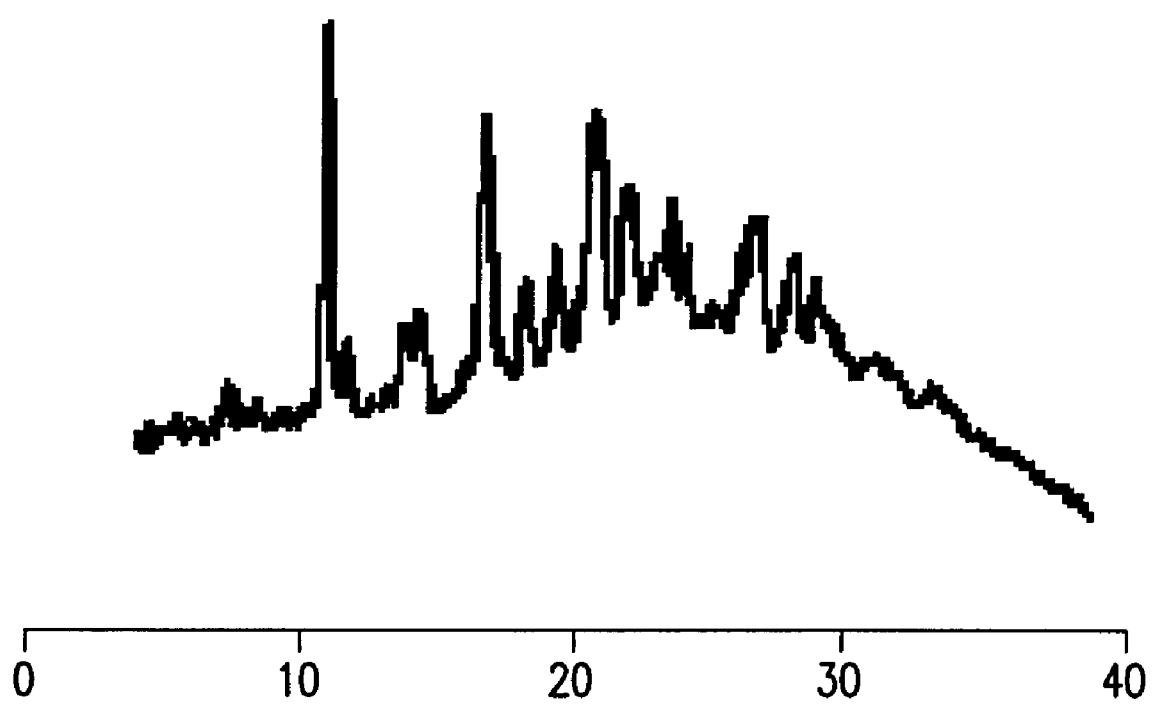
FIG. 3 is a characteristic powder x-ray diffraction spectrum of atomoxetine hydrochloride Form C.
Figure 4:
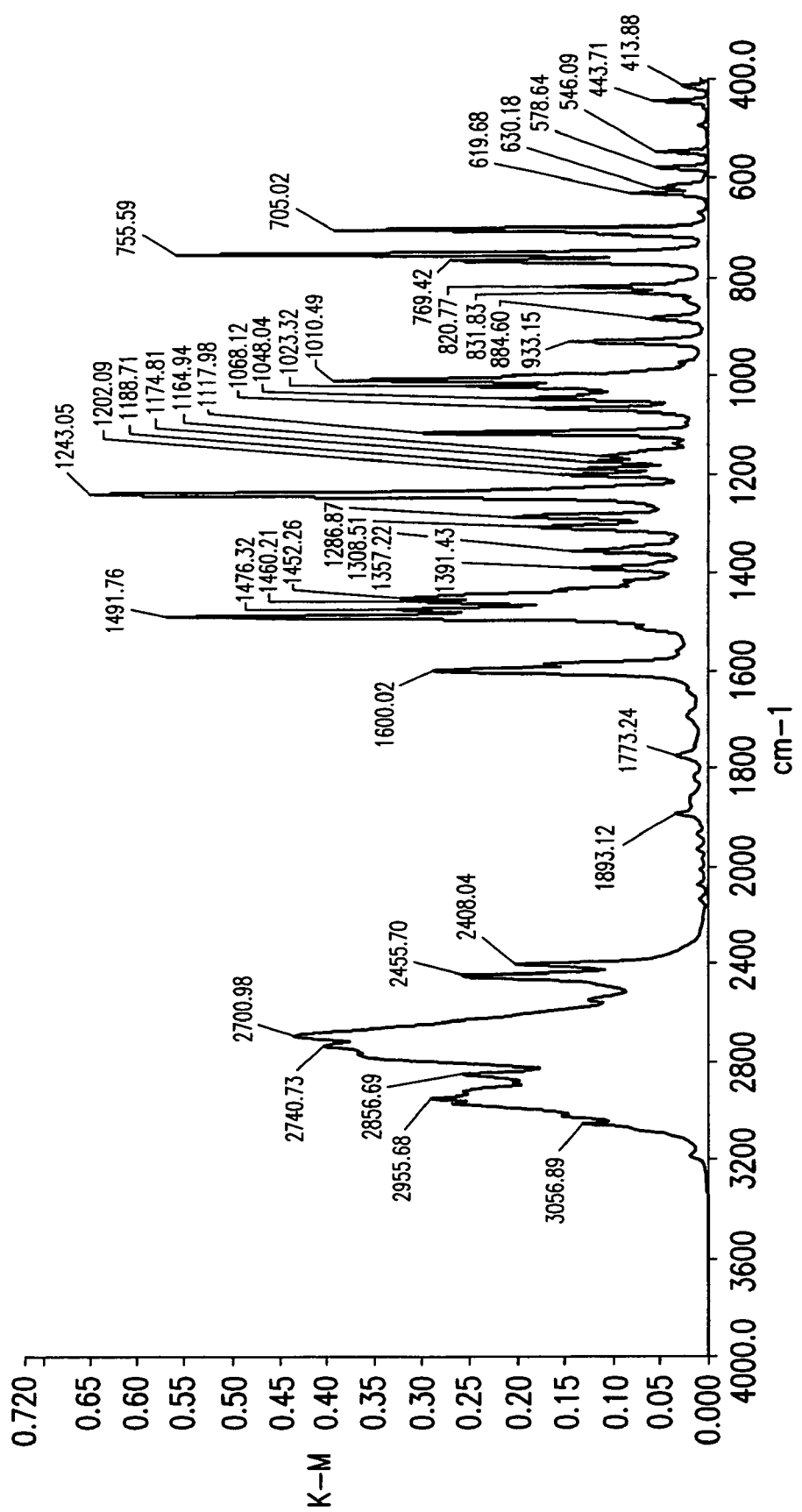
FIG. 4 is a characteristic infrared (IR) absorption spectrum of atomoxetine hydrochloride Form A.
Figure 8:
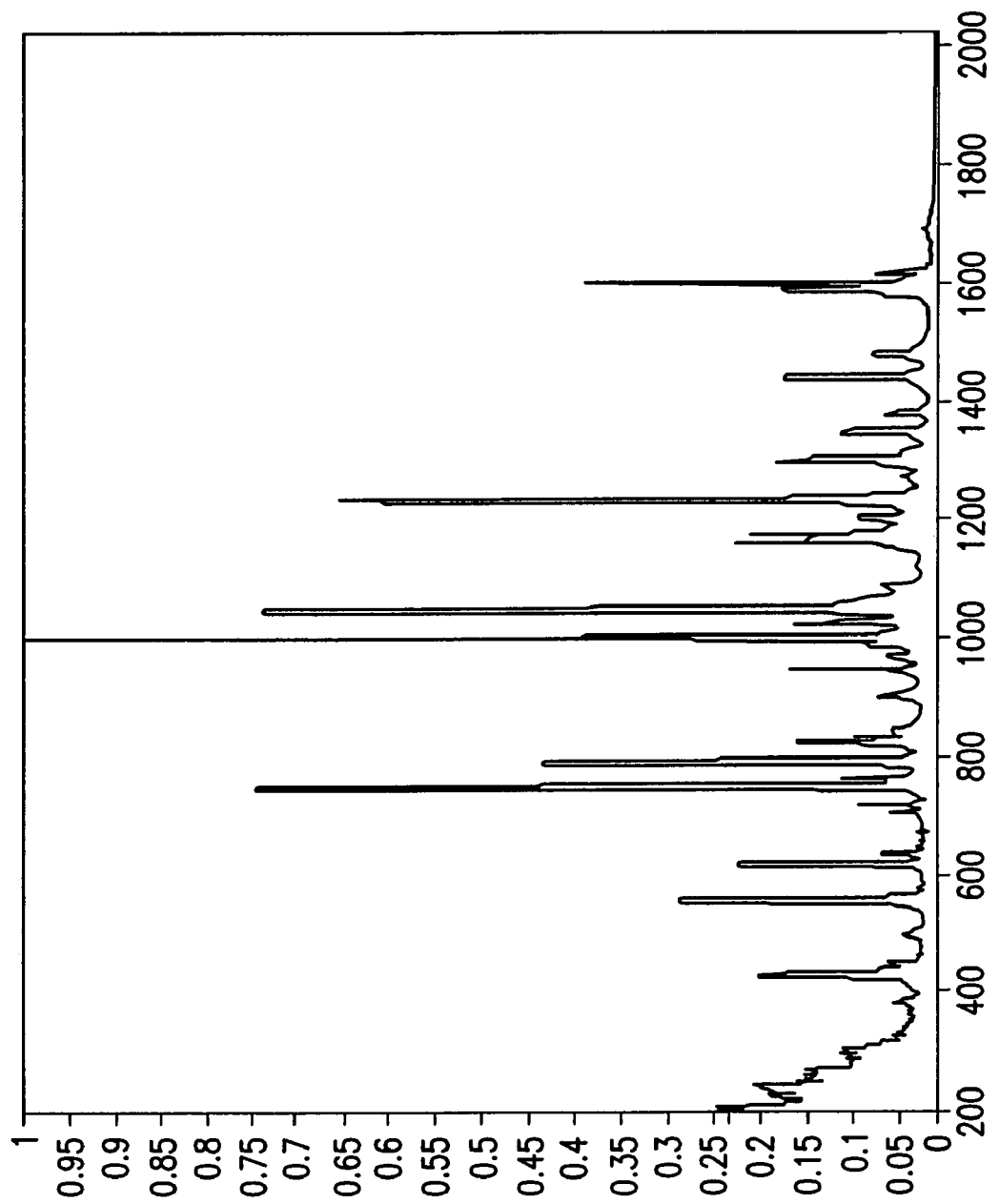
FIG. 8 is a characteristic Raman absorption spectrum spectrum of atomoxetine hydrochloride Form C.

The present invention provides a crystalline form of atomoxetine hydrochloride, denominated Form C, characterized by an x-ray powder diffraction pattern having peaks at about 10.1, 16.4, 18.2 and 25.1±0.2 degrees two-theta. Form C maybe further characterized by an x-ray powder diffraction pattern having peaks at about 11.1, 19.0, 20.9, 21.4, 22.1, 23.0, 23.6, 25.7, 26.8, 27.3, 29.0, 30.2, 31.1, 31.9, and 33.4±0.2 degrees two-theta, substantially as depicted in FIG. 3. Form C may be also characterized by a Raman absorption spectrum substantially as depicted in FIG. 8.

Atomoxetine hydrochloride form C may be further characterized by a melting point of about 168° C. The DSC thermogram of atomoxetine hydrochloride Form C shows a sharp endothermic melting peak followed by decomposition at about 210° C. Thermal weight change measurements indicated a weight loss of about 1.7%.

Atomoxetine hydrochloride Form C may be substantially free of Form A. In certain embodiments, Form C contains less than about 10%, preferably less than about 5%, and even more preferably less than about 1% (by weight) of Form A.

Atomoxetine hydrochloride Form C may be substantially free of Form B. In certain embodiments, Form C contains less than about 10%, preferably less than about 5%, and even more preferably less than about 1% (by weight) of Form B.

The invention also provides a process for making atomoxetine hydrochloride Form C comprising:
a) combining atomoxetine hydrochloride in a solution of water and acetone;
b) heating the mixture to a temperature of about 40° C. to about 60° C. for a sufficient time to dissolve the atomoxetine hydrochloride; and
c) removing the acetone and water to form atomoxetine hydrochloride Form C.

Preferably, the mixture is heated in step b) to a temperature of about 50° C. Preferably, the mixture in step b) is maintained for at least 2 hours. Preferably, the ratio of the water and acetone in the solution of step a) is 2:1. The acetic acid and water may be removed from the mixture by evaporation.

Pharmaceutical Compositions Containing Atomoxetine Hydrochloride Polymorphs

Another embodiment of the present invention is a pharmaceutical formulation comprising a therapeutically effective amount of an atomoxetine hydrochloride form selected from the group consisting of Form B, Form C, and mixtures thereof, combined with a pharmaceutically acceptable excipient or carrier.

Another embodiment of the present invention is a method for treating a patient suffering from attention deficit/hyperactivity disorder comprising the step of administering to the patient a pharmaceutical formulation comprising a therapeutically effective amount of atomoxetine hydrochloride selected from the group consisting of Form B, Form C, and mixtures thereof.

Alternatively, pharmaceutical formulations of the present invention may also contain mixtures of the crystalline polymorphs of atomoxetine hydrochloride disclosed herein.

In addition to the active ingredient(s), the pharmaceutical formulations of the present invention may contain one or more excipients. Excipients are added to the formulation for a variety of purposes.

Diluents may be added to the formulations of the present invention. Diluents increase the bulk of a solid pharmaceutical composition, and may make a pharmaceutical dosage form containing the composition easier for the patient and care giver to handle. Diluents for solid compositions include, for example, microcrystalline cellulose (e.g., AVICEL®), microfine cellulose, lactose, starch, pregelatinized starch, calcium carbonate, calcium sulfate, sugar, dextrates, dextrin, dextrose, dibasic calcium phosphate dihydrate, tribasic calcium phosphate, kaolin, magnesium carbonate, magnesium oxide, maltodextrin, mannitol, polymethacrylates (e.g., EUDRAGIT®), potassium chloride, powdered cellulose, sodium chloride, sorbitol, and talc.

Solid pharmaceutical compositions that are compacted into a dosage form, such as a tablet, may include excipients whose functions include helping to bind the active ingredient and other excipients together after compression. Binders for solid pharmaceutical compositions include acacia, alginic acid, carbomer (e.g., carbopol), carboxymethylcellulose sodium, dextrin, ethyl cellulose, gelatin, guar gum, hydrogenated vegetable oil, hydroxyethyl cellulose, hydroxypropyl cellulose (e.g., KLUCEL®), hydroxypropyl methyl cellulose (e.g., METHOCEL®), liquid glucose, magnesium aluminum silicate, maltodextrin, methylcellulose, polymethacrylates, povidone (e.g., KOLLIDON®, PLASDONE®), pregelatinized starch, sodium alginate, and starch.

The dissolution rate of a compacted solid pharmaceutical composition in the patient's stomach may be increased by the addition of a disintegrant to the composition. Disintegrants include alginic acid, carboxymethylcellulose calcium, carboxymethylcellulose sodium (e.g., AC-DI-SOL®, PRIMELLOSE®), colloidal silicon dioxide, croscarmellose sodium, crospovidone (e.g., KOLLIDON®, POLYPLASDONE®), guar gum, magnesium aluminum silicate, methyl cellulose, microcrystalline cellulose, polacrilin potassium, powdered cellulose, pregelatinized starch, sodium alginate, sodium starch glycolate (e.g., EXPLOTAB®), and starch.

Glidants can be added to improve the flowability of a non-compacted solid composition and to improve the accuracy of dosing. Excipients that may function as glidants include colloidal silicon dioxide, magnesium trisilicate, powdered cellulose, starch, talc, and tribasic calcium phosphate.

When a dosage form such as a tablet is made by the compaction of a powdered composition, the composition is subjected to pressure from a punch and dye. Some excipients and active ingredients have a tendency to adhere to the surfaces of the punch and dye, which can cause the product to have pitting and other surface irregularities. A lubricant can be added to the composition to reduce adhesion and ease the release of the product from the dye. Lubricants include magnesium stearate, calcium stearate, glyceryl monostearate, glyceryl palmitostearate, hydrogenated castor oil, hydrogenated vegetable oil, mineral oil, polyethylene glycol, sodium benzoate, sodium lauryl sulfate, sodium stearyl fumarate, stearic acid, talc, and zinc stearate.

Flavoring agents and flavor enhancers make the dosage form more palatable to the patient. Common flavoring agents and flavor enhancers for pharmaceutical products that may be included in the composition of the present invention include maltol, vanillin, ethyl vanillin, menthol, citric acid, fumaric acid, ethyl maltol, and tartaric acid.

Solid and liquid compositions may also be dyed using any pharmaceutically acceptable colorant to improve their appearance and/or facilitate patient identification of the product and unit dosage level.

The present invention is not intended to encompass true solutions of atomoxetine hydrochloride whereupon the crystal structure of the novel crystalline forms and the properties that characterize the novel crystalline forms of atomoxetine hydrochloride of the present invention are lost. However, the use of the novel forms to prepare such solutions (e.g., so as to deliver atomoxetine hydrochloride in a liquid pharmaceutical formulation) is considered to be within the contemplation of the invention.

In liquid pharmaceutical compositions prepared using the crystalline forms of the present invention, atomoxetine hydrochloride and any other solid excipients are dissolved or suspended in a liquid carrier such as water, vegetable oil, alcohol, polyethylene glycol, propylene glycol, or glycerin.

Liquid pharmaceutical compositions may contain emulsifying agents to disperse uniformly throughout the composition an active ingredient or other excipient that is not soluble in the liquid carrier. Emulsifying agents that may be useful in liquid compositions of the present invention include, for example, gelatin, egg yolk, casein, cholesterol, acacia, tragacanth, chondrus, pectin, methyl cellulose, carbomer, cetostearyl alcohol, and cetyl alcohol.

Liquid pharmaceutical compositions may also contain a viscosity enhancing agent to improve the mouth-feel of the product and/or coat the lining of the gastrointestinal tract. Such agents include acacia, alginic acid bentonite, carbomer, carboxymethylcellulose calcium or sodium, cetostearyl alcohol, methyl cellulose, ethylcellulose, gelatin guar gum, hydroxyethyl cellulose, hydroxypropyl cellulose, hydroxypropyl methyl cellulose, maltodextrin, polyvinyl alcohol, povidone, propylene carbonate, propylene glycol alginate, sodium alginate, sodium starch glycolate, starch tragacanth, and xanthan gum.

Sweetening agents such as sorbitol, saccharin, sodium saccharin, sucrose, aspartame, fructose, mannitol, and invert sugar may be added to improve the taste.

Preservatives and chelating agents such as alcohol, sodium benzoate, butylated hydroxyl toluene, butylated hydroxyanisole, and ethylenediamine tetraacetic acid may be added at levels safe for ingestion to improve storage stability.

A liquid composition may also contain a buffer such as guconic acid, lactic acid, citric acid or acetic acid, sodium guconate, sodium lactate, sodium citrate, or sodium acetate. Selection of excipients and the amounts used may be readily determined by the formulation scientist based upon experience and consideration of standard procedures and reference works in the field.

The solid compositions of the present invention include powders, granulates, aggregates and compacted compositions. The dosages include dosages suitable for oral, buccal, rectal, parenteral (including subcutaneous, intramuscular, and intravenous), inhalant and ophthalmic administration. Although the most suitable administration in any given case will depend on the nature and severity of the condition being treated, the most preferred route of the present invention is oral. The dosages may be conveniently presented in unit dosage form and prepared by any of the methods well-known in the pharmaceutical arts.

Dosage forms include solid dosage forms like tablets, powders, capsules, suppositories, sachets, troches and lozenges, as well as liquid syrups, suspensions and elixirs.

The dosage of STRATTERA® may be used as guidance. The oral dosage form of the present invention is preferably in the form of an oral capsule or tablet having a dosage of about 5 mg to about 160 mg, more preferably from about 20 mg to about 80 mg, and most preferably capsules or tablets of 10, 18, 20, 25, 40, 60 and 80 mg. Daily dosages may include 1, 2, or more capsules per day.

The dosage form of the present invention may be a capsule containing the composition, preferably a powdered or granulated solid composition of the invention, within either a hard or soft shell. The shell may be made from gelatin and optionally contain a plasticizer such as glycerin and sorbitol, and an opacifying agent or colorant.

A composition for tableting or capsule filling may be prepared by wet granulation. In wet granulation, some or all of the active ingredients and excipients in powder form are blended and then further mixed in the presence of a liquid, typically water, that causes the powders to clump into granules. The granulate is screened and/or milled, dried and then screened and/or milled to the desired particle size. The granulate may then be tableted, or other excipients may be added prior to tableting, such as a glidant and/or a lubricant.

A tableting composition may be prepared conventionally by dry blending. For example, the blended composition of the actives and excipients may be compacted into a slug or a sheet and then comminuted into compacted granules. The compacted granules may subsequently be compressed into a tablet.

As an alternative to dry granulation, a blended composition may be compressed directly into a compacted dosage form using direct compression techniques. Direct compression produces a more uniform tablet without granules. Excipients that are particularly well suited for direct compression tableting include microcrystalline cellulose, spray dried lactose, dicalcium phosphate dihydrate and colloidal silica. The proper use of these and other excipients in direct compression tableting is known to those in the art with experience and skill in particular formulation challenges of direct compression tableting.

A capsule filling of the present invention may comprise any of the aforementioned blends and granulates that were described with reference to tableting, however, they are not subjected to a final tableting step.

The active ingredient and excipients may be formulated into compositions and dosage forms according to methods known in the art.

It is not necessary that the formulations of the present invention contain only one crystalline form of atomoxetine hydrochloride. The crystalline forms of the present invention may be used in pharmaceutical formulations or compositions as single components or mixtures together with other crystalline forms of atomoxetine hydrochloride or with amorphous atomoxetine hydrochloride. However, it is preferred that the pharmaceutical formulations or compositions of the present invention contain 25-100% by weight, especially 50-100% by weight, of at least one of the novel forms, based on the total amount of atomoxetine hydrochloride in the formulation or composition. Preferably, such an amount of the novel crystalline form of atomoxetine hydrochloride is 75-100% by weight, especially 90-100% by weight. Highly preferred is an amount of 95-100% by weight.

Experimental

Powder x-ray diffraction data were obtained by ARL X-Ray powder diffractometer model X'TRA-030, Peltier detector, round standard aluminum sample holder with round zero background quartz plate was used. Scanning parameters: range: 2-40 deg. 2θ, continuous scan, rate: 3 deg./min. The accuracy of peak positions was defined as +/−0.2 degrees due to such experimental differences as instrumentation, sample preparations etc. Data were obtained with a Bruker D8 Discover equipped with a xyz translation stage (with x, y, z travel of 100 mm, 150 mm and 100 mm, respectively). The x-ray detector was a high-performance HI-STAR two-dimensional detector that was set to 15 cm from the centre of the goniometer. At this distance, the detector has a typical FWHM of 0.15-0.2 degrees in 2θ. The x-ray generator was typically set to 40 KV and 40 mA. The data was collected in one frame with a typical data acquisition time of 3 minutes. The 2θ range covered by the HI-STAR detector is from 4.5 to 39.5 degrees. The sample is typically oscillated in the y direction (perpendicular to the x-ray travel direction) with oscillation amplitude of ±2-3 mm. Omega-scan (rocking the x-ray source and the detector synchronously) was also used occasionally to reduce preferred orientation in samples that were producing very spotty diffraction patterns. Crystals grown on a universal substrate were analyzed either uncrushed or crushed. The crushing of crystalline samples was achieved with a pneumatic compactor that has 96 pins whose diameter is 0.25 inches, sufficient to encompass the area of the samples. The force on each pin was about 12 lb. Epoch software was used to facilitate the translation of the stage to the elements of interest and a joystick to control translation and a knob to adjust the Z height were used to focus the beam on samples of interest. Epoch then stored the images and coordinates of each of the user specified locations to the database. Epoch was also used to control the data acquisition and stored the acquisition parameters, area plots, and 2-theta plots to the database as one experiment.

The differential scanning thermograms (DSC) were obtained using a DSC $822^e$/700, Mettler Toledo. Typical sample weight was approximately 3-5 mg. The samples were heated to 30-350° C. at a rate of 10° C./min. and purged with nitrogen gas at a flow rate of 40 ml/min. Standard crucibles used had 3 small holes.

Thermal weight change measurements were made on a TGA 2950 Thermogravimetric analyzer by TA Instruments. Samples of 0.1-2 mg were placed in an aluminum pan and placed in the device. The data was collected from about 50 to about 350° C. at a rate of 10° C./min.

The infrared (IR) Raman spectroscopy experiments were performed with a JY/Horiba LabRam spectrometer. The excitation laser was a HeNe laser operating at 632.8 nm. The beam was focused onto the sample through the objective of an Olympus BX microscope. The microscope was equipped with crossed polarizing filters so that birefringence images could be used to facilitate the identification of crystalline material. Typically, the laser spot was sufficiently narrow as to allow the acquisition of the Raman spectra from individual crystals. Epoch software was used to facilitate the translation of the stage to the elements of interest and a joystick to control translation and a knob to adjust the Z height were used to focus the beam on samples of interest. Epoch then stored the images and coordinates of each of the user specified locations, including multiple locations per element, to the database as a mapping experiment. The software then executed a sequence so that Raman spectra were obtained for each set of coordinates defined in the mapping experiment. The scattered photons were collected at 180 degrees to the incident beam, the laser line was removed with a holographic notch filter, and the light was then separated with a grating and imaged onto a CCD. The spectra were collected at either a single grating position or the grating was scanned to collect signal over a larger Raman shift. Data collection times ranged from 10 seconds to several minutes depending on the scattering cross section of the sample. The spectra and acquisition parameters were then stored to the database for analysis.

FT-IR Spectroscopy was performed on Perkin-Elmer spectrum—One spectrophotometer. The samples were analyzed using diffuse reflectance technique (DRIFT). The samples were finely ground with Potassium Bromide and the spectrum was recorded using Potassium Bromide as background in a diffuse reflectance accessory. Scanning parameters were: range: 4000-400 cm-1, 16 scans, resolution:4.0 cm-1.z The photomicrograph of atomoxetine hydrochloride Form A was taken with Zeiss Axiolab Pol polarization microscope. The magnification was 200—1 scale unit corresponds to 10 micrometer.

Having described the invention with reference to certain preferred embodiments, other embodiments will become apparent to one skilled in the art from consideration of the specification. The invention is further defined by reference to the following examples describing in detail the preparation of the composition and methods of use of the invention. It will be apparent to those skilled in the art that many modifications, both to materials and methods, may be practiced without departing from the scope of the invention.

EXAMPLES

Preparation of Atomoxetine Hydrochloride Form A

Example 1

Atomoxetine HCl Form B (0.2 g, 0.0006854 mol) was mixed with 2 ml of acetone and stirred for 20 hours at 20-25° C. The solid was filtered and then washed with a few milliliters of dioxane and dried at room temperature to yield polymorph A.

Example 2

Ten grams (0.03427 mol) of atomoxetine HCl were mixed with a mixture of 180 ml of acetic acid/ethyl acetate (ratio 1:2) at room temperature. Most of the solvent was distilled off by under vacuum distillation at T<30° C. The solution was let to stand and after 4 days two crops of solid were collected and dried under vacuum at room temperature.

Example 3

Ten grams (0.03427 mol) of atomoxetine HCl were mixed with 33 ml of water at 50° C. The solution was cooled at 20-25° C. and a solid precipitated. The solid was collected by filtration and dried under vacuum at room temperature.

Example 4

Ten grams (0.03427 mol) of atomoxetine HCl was mixed with 33 ml of water at 50° C. A small amount of solvent was distilled off by distillation under vacuum at 50° C. A solid precipitated, and was stirred at room temperature. The solid was collected by filtration and dried under vacuum at room temperature.

Example 5

Five grams (0.01713 mol) of atomoxetine HCl were mixed with 30 ml of methanol at 50° C. Solvent was distilled off by distillation under vacuum at 50° C. until the solution became turbid. At room temperature a solid precipitated, and was collected by filtration and dried under vacuum at room temperature to yield polymorph A.

Example 6

Two grams (0.00741 mol) of atomoxetine free base were mixed at room temperature with 18 ml of a mixture of iso-propyl alcohol/methyl-t-butyl ether (ratio of 1:2). The temperature was kept at 20-25° C. by means of water-ice bath cooling while 0.81 g of aqueous (37%) hydrogen chloride was dropped into the obtained solution. When the solid crystallized, the slurry was stirred for 1 hour at 20-25° C. The solid was then collected by filtration, washed with methyl-t-butyl ether, and dried under vacuum at 45° C. for 2 hours.

Example 7

Two grams (0.00741 mol) of atomoxetine free base were mixed at room temperature with 18 ml of a mixture of iso-propyl alcohol/methyl-t-butyl ether (ratio of 1:2). The temperature was kept at 20-25° C. by means of water-ice bath cooling while gaseous hydrogen chloride was bubbled into the obtained solution. The solid crystallized and the slurry was stirred for 1 hour at 20-25° C. The solid was collected by filtration, washed with methyl-t-butyl ether, and dried under vacuum at 45° C. for 2 hours.

Example 8

Two grams (0.00741 mol) of atomoxetine free base were mixed at room temperature with 18 ml of ethyl acetate. The temperature was kept at 20-25° C. by means of water-ice bath cooling, while 0.81 g of aqueous (37%) hydrogen chloride was dropped into the obtained solution. The solid crystallized and the slurry was stirred for 1 hour at 20-25° C. The solid was collected by filtration, washed with ethyl acetate, and dried under vacuum at 45° C. for 2 hours.

Example 9

Two grams (0.00741 mol) of atomoxetine free base were mixed at room temperature with 18 ml of ethyl acetate. The temperature was kept at 20-25° C. by means of water-ice bath cooling while gaseous hydrogen chloride was bubbled into the obtained solution. The solid crystallized and the slurry was stirred for 1 hour at 20-25° C. The solid was then collected by filtration, washed with ethyl acetate, and dried under vacuum at 45° C. for 2 hours.

Example 10

Two grams (0.00741 mol) of atomoxetine free base were mixed at room temperature with 18 ml of iso-propyl alcohol. The temperature was kept at 20-25° C. by means of water-ice bath cooling while 0.81 g of aqueous (37%) hydrogen chloride was dropped into the obtained solution. The solid crystallized and the slurry was stirred for 1 hour at 20-25° C. The solid was collected by filtration, washed with iso-propyl alcohol, and dried under vacuum at 45° C. for 2 hours.

Example 11

Two grams (0.00741 mol) of atomoxetine free base were mixed at room temperature with 18 ml of iso-propyl alcohol. The temperature was kept at 20-25° C. by means of water-ice bath cooling while gaseous hydrogen chloride was bubbled into the obtained solution. The solid crystallized and the slurry stirred for 1 hour at 20-25° C. The solid was collected by filtration, washed with iso-propyl alcohol, and dried under vacuum at 45° C. for 2 hours.

Example 12

Atomoxetine free base (32.9 g, 0.1169 mol) was mixed at room temperature with 376.3 ml of ethyl acetate. Keeping the temperature at 15-20° C. by means of water-ice bath cooling, 12.7 g of aqueous (37%) hydrogen chloride was dropped into the obtained solution. The solid crystallized and the slurry was stirred for 1 hour at 5° C. The solid was collected by filtration, washed with ethyl acetate, and dried under vacuum at 45° C. for 18 hours.

Preparation of Atomoxetine Hydrochloride Form B

Example 13

Two grams (0.00491) of atomoxetine (S)-(+)-mandelate were mixed at room temperature with 10 ml of toluene and 1 ml of MeOH and under stirring was heated to about 60° C. Keeping the temperature at 60° C. by means of oil bath heating, gaseous hydrogen chloride was bubbled into the obtained solution. The solution was cooled at 20-25° C. and a solid crystallized. The slurry was stirred for 1 hour at 0° C., and then the solid collected by filtration, washed with toluene, and dried under vacuum at 45° C. for 5 hours.

Example 14

50 mg of atomoxetine HCl were mixed with 4 ml of water and 2 ml of acetic acid. The mixture was heated at 50° C. for 2 hours until it became clear. The solution was evaporated and the resulting Form B crystals were collected.

Preparation of Atomoxetine Hydrochloride Form C

Example 15

50 mg of atomoxetine HCl were mixed with 4 ml of water and 2 ml of acetone. The mixture was heated at 50° C. for 2 hours until it became clear. The solution was evaporated and the resulting atomoxetine Form C was collected.

Table 1 shows the DSC data for the atomoxetine polymorphs obtained from the examples above:

TABLE 1

| EXPERIMENT | Cryst. form | DSC mp |
| --- | --- | --- |
| Example 1 | A | 169.4 |
| Example 2 | A | 169.3 |
| Example 2 | A | 168.9 |
| Example 3 | A | 169.6 |
| Example 4 | A | 169.6 |
| Example 5 | A | 169.8 |
| Example 6 | A | 168.1 |
| Example 7 | A | 167.3 |
| Example 8 | A | 168.5 |
| Example 9 | A | 167.3 |
| Example 10 | A | 168.7 |
| Example 11 | A | 168.5 |
| Example 12 | A | 164.0 + 169.8 |
| Example 13 | B | 163.2 |
| Example 14 | B | 168.3 |
| Example 15 | C | 168.2 |

Samples that have a small additional peak in DSC before melting may contain either a small amount of form B or a small amount of the intermediate.

It should be understood that some modification, alteration, and substitution is anticipated and expected from those skilled in the art without departing from the teachings of the invention. Accordingly, it is appropriate that the following claims be construed broadly and in a manner consistent with the scope and spirit of the invention.

What is claimed is:

1. A process for the preparation of a crystalline form of atomoxetine hydrochloride characterized by a powder x-ray diffraction pattern having peaks at about 13.7, 17.3, 18.7, 21.1, 22.6, 24.0, 27.3, 28.4 and 29.3±0.2 degrees two-theta comprising the steps of:
    a) combining atomoxetine hydrochloride Form B with acetone to obtain a mixture; and
    b) maintaining the mixture for a sufficient time to obtain the crystalline form of atomoxetine hydrochloride characterized by a powder x-ray diffraction pattern having peaks at about 13.7, 17.3, 18.7, 21.1, 22.6, 24.0, 27.3, 28.4 and 29.3±0.2 degrees two-theta.

2. The process of claim 1, wherein the mixture is maintained for about 20 hours.

3. A process for the preparation of a crystalline form of atomoxetine hydrochloride characterized by a powder x-ray diffraction pattern having peaks at about 13.7, 17.3, 18.7, 21.1, 22.6, 24.0, 27.3, 28.4 and 29.3±0.2 degrees two-theta comprising the steps of:
    a) combining atomoxetine hydrochloride with water at a temperature of about 40° C. to about 60° C. to obtain a mixture;
    b) cooling the mixture to room temperature to obtain a precipitate; and
    c) recovering the crystalline atomoxetine hydrochloride characterized by a powder x-ray diffraction pattern having peaks at about 13.7, 17.3, 18.7, 21.1, 22.6, 24.0, 27.3, 28.4 and 29.3±0.2 degrees two-theta.

4. The process of claim 3, wherein the atomoxetine hydrochloride and water in step a) are heated to a temperature of about 50° C.

5. A process for the preparation of a crystalline form of atomoxetine hydrochloride characterized by a powder x-ray diffraction pattern having peaks at about 13.7, 17.3, 18.7, 21.1, 22.6, 24.0, 27.3, 28.4 and 29.3±0.2 degrees two-theta comprising the steps of:
    a) combining atomoxetine hydrochloride with a solvent selected from water, methanol, and a mixture of acetic acid and ethyl acetate, at a temperature ranging from room temperature to about 60° C. to obtain a mixture;
    b) removing at least some of the solvent until a precipitate forms; and
    c) recovering atomoxetine hydrochloride characterized by a powder x-ray diffraction pattern having peaks at about 13.7, 17.3, 18.7, 21.1, 22.6, 24.0, 27.3, 28.4 and 29.3±0.2 degrees two-theta.

6. The process of claim 5, wherein the ratio of the acetic acid:ethyl acetate mixture is 1:2.

7. The process of claim 5, wherein the solvent is removed by distillation.

8. A crystalline form of atomoxetine hydrochloride, characterized by data selected from: an x-ray powder diffraction pattern having peaks at about 11.5, 17.1, 19.8, 21.3, 22.5, 23.6, 24.6, 27.5 and 28.5±0.2 degrees two-theta; and an infrared absorption spectrum having peaks at about 2761, 1596, 1493, 1234, 768, and 711 $cm^{-1}$.

9. The crystalline form of atomoxetine hydrochloride of claim 8, characterized by an x-ray powder diffraction pattern having peaks at about 11.5, 17.1, 19.8, 21.3, 22.5, 23.6, 24.6, 27.5 and 28.5±0.2 degrees two-theta.

10. The crystalline form of atomoxetine hydrochloride of claim 9, further characterized by an x-ray powder diffraction pattern having peaks at about 7.8, 8.9, 12.2, 14.3, 14.9, 18.7, 26.0, 29.4, 29.9 and 31.2±0.2 degrees two-theta.

11. The crystalline form of atomoxetine hydrochloride of claim 8, characterized by an infrared absorption spectrum having peaks at about 2761, 1596, 1493, 1234, 768, 711 cm$^{-1}$.

12. The crystalline form of atomoxetine hydrochloride of claim 11, further characterized by an infrared absorption spectrum having peaks at about 3017, 2958, 2928, 2845, 2508, 2442, 1479, 1460, 1433, 1371, 1358, 1285, 1207, 1192, 1175, 1164, 1137, 1118, 1072, 1047, 1037, 1023, 1010, 963, 931, 861, 755, 605, 568, and 535 cm$^{-1}$.

13. The crystalline form of atomoxetine hydrochloride of claim 8, having less than about 10% (by weight) Form A.

14. The crystalline form of atomoxetine hydrochloride of claim 13, having less than about 5% (by weight) Form A.

15. The crystalline form of atomoxetine hydrochloride of claim 14, having less than about 1% (by weight) Form A.

16. A process for the preparation of the crystalline form of atomoxetine hydrochloride, characterized by data selected from: an x-ray powder diffraction pattern having peaks at about 11.5, 17.1, 19.8, 21.3, 22.5, 23.6, 24.6, 27.5 and 28.5±0.2 degrees two-theta; and an infrared absorption spectrum having peaks at about 2761, 1596, 1493, 1234, 768, and 711 cm$^{-1}$, the process comprising the steps of:
   a) combining atomoxetine-(S)-(+)-mandelate with toluene and methanol to obtain a reaction mixture;
   b) heating the reaction mixture to a temperature of about 60° C.;
   c) combining the reaction mixture with gaseous hydrogen chloride;
   d) cooling the reaction mixture of step c) to a temperature of about 20° C. to about 25° C. for a sufficient amount of time for a slurry to form; and
   e) recovering the crystalline form of atomoxetine hydrochloride from the slurry.

17. The process of claim 16, wherein the slurry formed in step d) is further cooled to about 0° C.

18. A process for the preparation of a crystalline form of atomoxetine hydrochloride, characterized by data selected from: an x-ray powder diffraction pattern having peaks at about 11.5, 17.1, 19.8, 21.3, 22.5, 23.6, 24.6, 27.5 and 28.5±0.2 degrees two-theta; and an infrared absorption spectrum having peaks at about 2761, 1596, 1493, 1234, 768, and 711 cm$^{-1}$, the process comprising the steps of:
   a) combining atomoxetine hydrochloride in a solution of water and acetic acid;
   b) heating the mixture to a temperature of about 40° C. to about ° C. for a sufficient time to dissolve the atomoxetine hydrochloride; and
   c) removing the acetic acid and water to form the crystalline form of atomoxetine hydrochloride.

19. The process of claim 18, wherein the mixture is heated in step b) to a temperature of about 50° C.

20. The process of claim 18, wherein the mixture in step b) is maintained for at least 2 hours.

21. The process of claim 18, wherein the ratio of the water and acetic acid in the solution of step a) is 2:1.

22. The process of claim 18, wherein the acetic acid and water are removed by evaporation.

23. A crystalline form of atomoxetine hydrochloride, characterized by an x-ray powder diffraction pattern having peaks at about 10.1, 16.4, 18.2 and 25.1±0.2 degrees two-theta.

24. The crystalline form of atomoxetine hydrochloride of claim 23, further characterized by an x-ray powder diffraction pattern having peaks at about 11.1, 19.0, 20.9, 21.4, 22.1, 23.0, 23.6, 25.7, 26.8, 27.3, 29.0, 30.2, 31.1, 31.9, and 33.4±0.2 degrees two-theta.

25. The crystalline form of atomoxetine hydrochloride of claim 23, having less than about 10% (by weight) Form A.

26. The crystalline form of atomoxetine hydrochloride of claim 25, having less than about 5% (by weight) Form A.

27. The crystalline form of atomoxetine hydrochloride of claim 26, having less than about 1% (by weight) Form A.

28. A process for the preparation of a crystalline form of atomoxetine hydrochloride characterized by an x-ray powder diffraction pattern having peaks at about 10.1, 16.4, 18.2 and 25.1±0.2 degrees two-theta, the process comprising the steps of:
   a) combining atomoxetine hydrochloride in a solution of water and acetone;
   b) heating the mixture to a temperature of about 40° C. to about 60° C. for a sufficient time to dissolve the atomoxetine hydrochloride; and
   c) removing the acetone and water to form the crystalline form of atomoxetine hydrochloride.

29. The process of claim 28, wherein the mixture is heated in step b) to a temperature of about 50° C.

30. The process of claim 28, wherein the mixture in step b) is maintained for at least 2 hours.

31. The process of claim 28, wherein the ratio of the water and acetone in the solution of step a) is 2:1.

32. The process of claim 28, wherein the acetone and water are removed by evaporation.

33. A pharmaceutical composition prepared by combining at least one pharmaceutically acceptable excipient with at least one of the crystalline forms of atomoxetine hydrochloride of any one of claims 8 and 23.

34. A method of treating attention deficit/hyperactivity disorder comprising administering the pharmaceutical composition of claim 33 to a patient in need thereof.

* * * * *